(12) United States Patent
Cheng

(10) Patent No.: US 12,210,011 B2
(45) Date of Patent: Jan. 28, 2025

(54) NANOPORE STRUCTURES

(71) Applicant: International Business Machines Corporation, Armonk, NY (US)

(72) Inventor: Kangguo Cheng, Schenectady, NY (US)

(73) Assignee: International Business Machines Corporation, Armonk, NY (US)

( * ) Notice: Subject to any disclaimer, the term of this patent is extended or adjusted under 35 U.S.C. 154(b) by 68 days.

(21) Appl. No.: 18/139,160

(22) Filed: Apr. 25, 2023

(65) Prior Publication Data

US 2023/0258622 A1 Aug. 17, 2023

Related U.S. Application Data

(62) Division of application No. 16/900,887, filed on Jun. 13, 2020, now Pat. No. 11,674,947.

(51) Int. Cl.
*G01N 33/487* (2006.01)
*B82Y 15/00* (2011.01)
*G01N 27/414* (2006.01)

(52) U.S. Cl.
CPC ... *G01N 33/48721* (2013.01); *G01N 27/4148* (2013.01); *B82Y 15/00* (2013.01); *H01L 2221/1063* (2013.01)

(58) Field of Classification Search
None
See application file for complete search history.

(56) References Cited

U.S. PATENT DOCUMENTS

| | | |
|---|---|---|
| 6,706,203 B2 | 3/2004 | Barth et al. |
| 7,195,780 B2 | 3/2007 | Dennis et al. |
| 7,879,734 B2 | 2/2011 | Fukutani et al. |
| 7,922,927 B2 | 4/2011 | Kamins et al. |
| 8,354,336 B2 | 1/2013 | Afzali-Ardakani et al. |
| 8,802,838 B2 | 8/2014 | Meller et al. |
| 8,828,138 B2 | 9/2014 | Bedell et al. |
| 10,416,147 B2 | 9/2019 | Yanagi et al. |
| 2017/0315109 A1 | 11/2017 | Alden et al. |
| 2019/0079048 A1 | 3/2019 | Cheng |

(Continued)

FOREIGN PATENT DOCUMENTS

| | | |
|---|---|---|
| EP | 2182996 B1 | 1/2013 |
| EP | 1820224 B1 | 4/2015 |
| KR | 1020130143429 A | 12/2013 |

OTHER PUBLICATIONS

List of IBM Patents or Applications Treated as Related, Apr. 25, 2023 (2 pages).

*Primary Examiner* — J. Christopher Ball

(74) *Attorney, Agent, or Firm* — Kelsey M. Skodje

(57) ABSTRACT

Nanopore structures are provided. In one aspect, a nanopore structure includes: an oxide shell surrounding a nanopore, wherein openings on both ends of the nanopore have a diameter D1, and a center of the nanopore has a diameter D2, wherein D1>D2. In another aspect, the nanopore structure includes: a first film disposed on a substrate; a second film disposed on the first film; at least one pore extending through the first film and the second film; a dielectric material disposed in the at least one pore; and a nanopore at a center of the dielectric material in the at least one pore, wherein a top opening to the nanopore has a first diameter d1, and a bottom opening to the nanopore has a second diameter d2, wherein d2>d1. Methods of forming the nanopore structures are also provided.

12 Claims, 12 Drawing Sheets

(56) References Cited

U.S. PATENT DOCUMENTS

2019/0092633 A1 3/2019 Johnson et al.
2019/0271660 A1 9/2019 Chan et al.
2021/0391223 A1 12/2021 Cheng back side etch to open bottoms of nanopores

NANOPORE STRUCTURES

FIELD OF THE INVENTION

The present invention relates to nanopore technology, and more particularly, to nanopore structures and techniques for formation thereof.

BACKGROUND OF THE INVENTION

Nanosized pores, or nanopores, have a variety of different applications. For instance, nanopores have been used to fabricate biosensors for deoxyribonucleic acid (DNA) sequencing.

Solid state nanopores are nanopores that are formed in a dielectric membrane. Solid state nanopores are an attractive technology as they have the potential to be integrated with semiconductor complementary metal-oxide semiconductor (CMOS) devices.

Conventionally nanopores are formed by depositing a thin film membrane on a silicon substrate, followed by patterning to form holes (the nanopores) in the film. A back side etch of the silicon substrate is then performed to open the nanopores. There are, however, some notable problems associated with forming nanopores by direct patterning. For instance, nanopores have a very small feature size (e.g., a diameter of less than 10 nanometers (nm)). It is very challenging to form such small features with direct patterning using a conventional etch such as reactive ion etching (RIE).

Further, direct patterning typically results in rough surfaces and variation in nanopore sizes. These rough surfaces and variation in nanopore sizes impact the accuracy of nanopore devices and thus compromise the performance of the nanopores devices.

Therefore, improved techniques for forming nanopores would be desirable.

SUMMARY OF THE INVENTION

The present invention provides nanopore structures and techniques for formation thereof. In one aspect of the invention, a nanopore structure is provided. The nanopore structure includes: an oxide shell surrounding a nanopore, wherein openings on both ends of the nanopore have a diameter D1, and a center of the nanopore has a diameter D2, wherein D1>D2.

In another aspect of the invention, another nanopore structure is provided. The nanopore structure includes: a first film disposed on a substrate; a second film disposed on the first film; at least one pore extending through the first film and the second film; an oxide material disposed in the at least one pore; and a nanopore at a center of the oxide material in the at least one pore, wherein a top opening to the nanopore has a first diameter d1, and a bottom opening to the nanopore has a second diameter d2, wherein d2>d1.

In yet another aspect of the invention, a method of forming a nanopore structure is provided. The method includes: forming a silicon germanium (SiGe) pillar on a substrate; annealing the SiGe pillar in an oxygen-containing ambient under conditions sufficient to form an oxide shell surrounding a condensed SiGe pillar core; and removing the condensed SiGe pillar core selective to the oxide shell to form a nanopore in the oxide shell.

In still yet another aspect of the invention, another method of forming a nanopore structure is provided. The method includes: depositing a first film on a substrate; depositing a second film on the first film; forming at least one pore extending through the first film and the second film, wherein the at least one pore has a diameter D1'; performing an etch of the first film to enlarge the at least one pore in the first film by an amount r, wherein following the etch the at least one pore has a diameter D1A' in the first film, and wherein D1A'>D1' by the amount r; and depositing a dielectric material into the at least one pore to form a nanopore at a center of the dielectric material, wherein the nanopore formed in the at least one pore has a diameter of 2r.

A more complete understanding of the present invention, as well as further features and advantages of the present invention, will be obtained by reference to the following detailed description and drawings.

DETAILED DESCRIPTION OF PREFERRED EMBODIMENTS

As provided above, direct patterning of pores with nanoscale dimensions, i.e., nanopores, is difficult with conventional etching processes and has some notable drawbacks such as surface roughness. Advantageously, provided herein are nanopore devices and techniques for fabrication thereof that do not rely on direct patterning of the nanopores. For instance, as will be described in detail below, in one exemplary embodiment an oxidation (condensation) process is used to form a nanopore(s) surrounded by a unique oxide shell. Further, embodiments are also provided herein where a pore size of the nanopores is controllable and thus not subject to any process variations.

Figure 1:
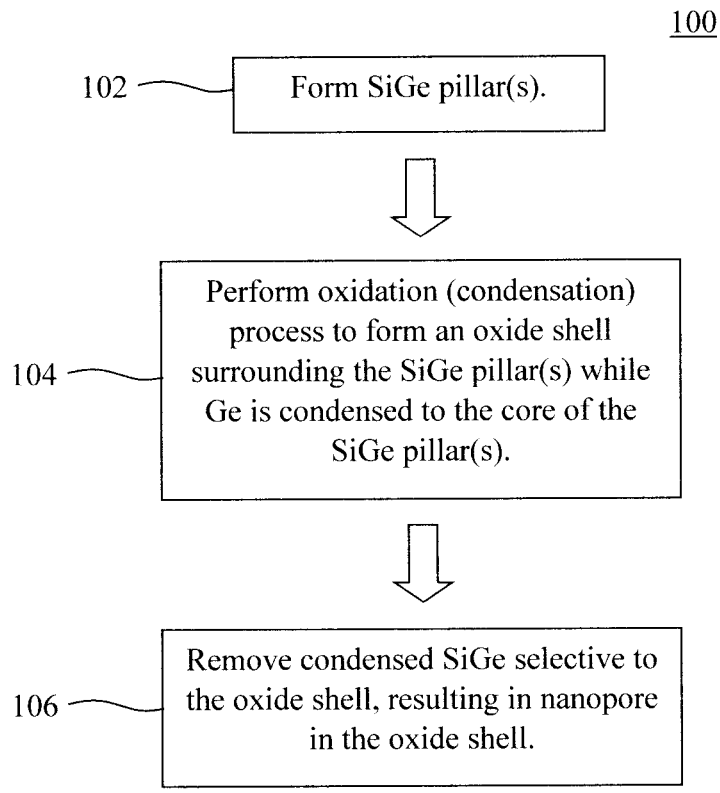
FIG. 1 is a diagram illustrating an exemplary methodology for forming a nanopores structure using an oxidation (condensation) process according to an embodiment of the present invention.

In a first exemplary embodiment, silicon germanium (SiGe) condensation is used to form a nanopore structure having a unique oxide shell. An overview of this SiGe condensation process for nanopore formation is now provided by way of reference to methodology 100 of FIG. 1.

As shown in step 102, at least one SiGe pillar is formed, e.g., on a silicon (Si) substrate. As will be described in detail below, the SiGe pillar(s) can be patterned in an epitaxial SiGe layer that has been grown on the substrate. The SiGe pillar(s) serves as the base structure for forming a nanopore(s) using an oxidation process.

Namely, as shown in step 104, a thermal oxidation process is used to form an oxide (i.e., SiOx) shell surrounding the SiGe pillar. In one embodiment, by way of this thermal oxidation process, the germanium (Ge) is condensed within the SiGe pillar core. Namely, as the Si atoms in the SiGe pillar are used to form the oxide shell, the percentage of Ge atoms in the SiGe pillar core increases. For instance, by way of example only, the as-patterned SiGe pillar(s) prior to oxidation can have from about 20% Ge to about 50% Ge and ranges therebetween. Following the oxidation process (condensation), the SiGe pillar(s) core can have from about 50% Ge to about 100% Ge (i.e., pure Ge) and ranges therebetween.

The oxidation process is carried out by annealing the SiGe pillar(s) in an oxygen-containing ambient under conditions sufficient to form the oxide (i.e., SiOx) shell surrounding the SiGe pillar core of condensed Ge. According to an exemplary embodiment, the conditions include a temperature of from about 400° C. to about 1200° C. and ranges therebetween, and a duration of from about 1 second to about 1 hour and ranges therebetween. The oxide process can be a dry oxidation, a wet oxidation, or an in-situ steam generation (ISSG) oxidation. The oxidation process can be a furnace oxidation, a rapid thermal oxidation (RTO), plasma oxidation, or any other suitable oxidation process. Depending on the oxide process condition, in some embodiments the oxide shell comprises substantially SiOx (silicon oxide) while in other embodiments, the oxide shell can include SiGeOx (silicon germanium oxide). For instance, dry oxidation at high temperatures (above 1000° C.) results in SiOx while wet oxidation at low temperatures (e.g., oxidation with water vapor at 500° C.) results in SiGeOx.

In step 106, the (condensed) SiGe pillar core is removed selective to the oxide shell. The result is a nanopore being formed in the oxide shell. By way of example only, etchants such as an aqueous solution containing ammonium and hydrogen peroxide, gas phase hydrogen chloride (HCl), vapor phase chlorine trifluoride ($ClF_3$), and other reactive clean processes (RCP) are selective for etching of SiGe versus Si. As will be described in detail below, the oxide shell formed by this process will have a unique 'barrel-shaped' cross-sectional configuration, and a nanopore that is wider at the openings at the ends of the nanopore than at its center (see below).

Figure 2:
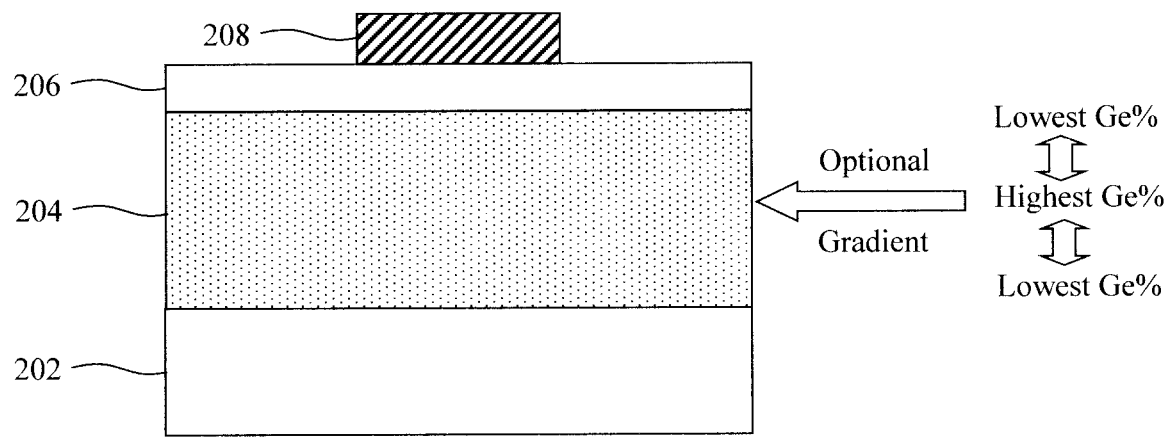
FIG. 2 is a cross-sectional diagram illustrating a silicon germanium (SiGe) layer having been deposited on a substrate, an optional silicon (Si) layer having been deposited onto the SiGe layer, and a patterned hardmask having been formed on the Si layer, if present, or directly on the SiGe layer according to an embodiment of the present invention.

An exemplary implementation of methodology 100 in the formation of a nanopore structure is now described by way of reference to FIGS. 2-8. As shown in FIG. 2, the process begins with a substrate 202 on which a SiGe layer 204 is deposited. According to an exemplary embodiment, substrate 202 is a bulk semiconductor wafer, such as a bulk silicon (Si), bulk germanium (Ge), bulk silicon germanium (SiGe) and/or bulk III-V semiconductor wafer. Other materials such as glass and ceramic can also be used. Alternatively, substrate 202 can be a semiconductor-on-insulator (SOI) wafer. A SOI wafer includes a SOI layer separated from an underlying substrate by a buried insulator. When the buried insulator is an oxide it is referred to herein as a buried oxide or BOX. The SOI layer can include any suitable semiconductor, such as Si, Ge, SiGe, and/or a III-V semiconductor. Substrate 202 may already have pre-built structures (not shown) such as transistors, diodes, capacitors, resistors, interconnects, wiring, etc.

By way of example only, the SiGe layer 204 can be epitaxially grown on the substrate 202. According to an exemplary embodiment, SiGe layer 204 has a thickness of from about 5 nanometers (nm) to about 10 nm and ranges therebetween. By way of example only, SiGe layer 204 can have a Ge percentage of from about 20% Ge to about 50% Ge and ranges therebetween. Besides epitaxy, other deposition techniques such as chemical vapor deposition (CVD), physical vapor deposition (PVD), sputtering, etc. can be used to form the SiGe layer 204.

Optionally, a silicon (Si) layer 206 is deposited onto SiGe layer 204. As will be described in detail below, use of Si layer 206 helps to ensure that a thicker oxide (i.e., SiOx) shell is produced in the middle portion of the SiGe pillar and a thinner oxide (i.e., SiOx) shell is produced at the Si/SiGe interfaces, resulting in the present cross-sectional barrel-shaped oxide shell configuration surrounding a nanopore that is wider at the openings at the ends of the nanopore than at its center (see below). By way of example only, optional Si layer 206 can be epitaxially grown on SiGe layer 204. According to an exemplary embodiment, Si layer 206 has a thickness of from about 1 nm to about 5 nm and ranges therebetween. The optional Si layer 206 can be epitaxially grown in the same epitaxy process as SiGe epitaxy growth.

In another exemplary embodiment, a SiGe layer with a varied germanium (Ge) concentration can be formed on the substrate 202. Specifically, the formation of the SiGe layer 204 can start with a low Ge concentration (e.g., 5% Ge %) and gradually increase Ge concentration as the deposition process continues. Once the thickness of the SiGe reaches a desired thickness (e.g., 5 nm with Ge % of 50%), the Ge concentration is then gradually reduced during the subsequent SiGe deposition processing. After such a deposition process, vertically the Ge % is highest in the middle of the SiGe layer 204 and lowest at the bottom (interface between SiGe layer 204 and substrate 202) and at the top of the SiGe layer 204. In the next step of oxidation processing, the higher Ge % in SiGe layer 204 will be oxidized faster, resulting in the barrel-shape oxide shell.

A patterned hardmask 208 is then formed on the Si layer 206, if present, or directly on the SiGe layer 204, marking the footprint and location of at least one SiGe pillar. Suitable hardmask materials include, but are not limited to, nitride hardmask materials such as silicon nitride (SiN), silicon oxynitride (SiON) and/or silicon carbide nitride (SiCN). Direct patterning can be used to form hardmask 208. Alternatively, the hardmask 208 can be formed by other suitable techniques, including but not limited to, sidewall image transfer (SIT), self-aligned double patterning (SADP), self-aligned quadruple patterning (SAQP), and other self-aligned multiple patterning (SAMP).

Figure 3:
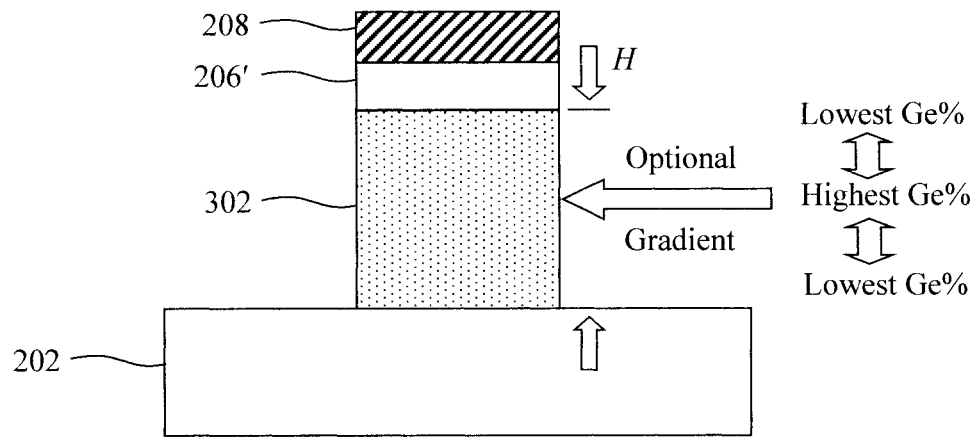
FIG. 3 is a cross-sectional diagram illustrating the pattern from the hardmask having been transferred to the Si layer, if present, and to the underlying SiGe layer, forming at least one SiGe pillar according to an embodiment of the present invention.

As shown in FIG. 3, the pattern from hardmask 208 is then transferred to Si layer 206, if present, and to the underlying SiGe layer 204, forming at least one SiGe pillar 302. A directional (anisotropic) etching process such as reactive ion etching (RIE) can be employed. If present, the patterned portion of Si layer 206 is now given the reference numeral 206'. While FIG. 3 provides a cross-sectional view, it is to be understood that SiGe pillar 302 is generally a rounded pillar-shaped structure which, as will be described in detail below, serves as the basis for forming a round nanopore. By way of example only, the SiGe pillar 302 has a diameter of from about 20 nm to about 50 nm and ranges therebetween.

As provided above, SiGe layer 204 can be formed from epitaxial SiGe having, e.g., a Ge percentage of from about 20% Ge to about 50% Ge and ranges therebetween. However, as will be described in detail below, the oxidation process used to form the oxide shell (of the nanopore) will condense the Ge in the SiGe pillar core. Further, based on the thickness of SiGe layer 204, according to an exemplary embodiment, SiGe pillar 302 has a height H of from about 5 nanometers (nm) to about 10 nm and ranges therebetween. See FIG. 3.

Also provided above, SiGe layer 204 can have a varied Ge % with a highest Ge % (vertically) in the middle portion of the SiGe layer 204 and a lowest Ge % at the bottom and top of the SiGe layer 204. In that case, because the oxidation rate depends on Ge % (the higher the Ge %, the higher the oxidation rate) a barrel shape oxide shell can be formed after oxidizing such SiGe pillar 302 with varied Ge %.

Figure 4:
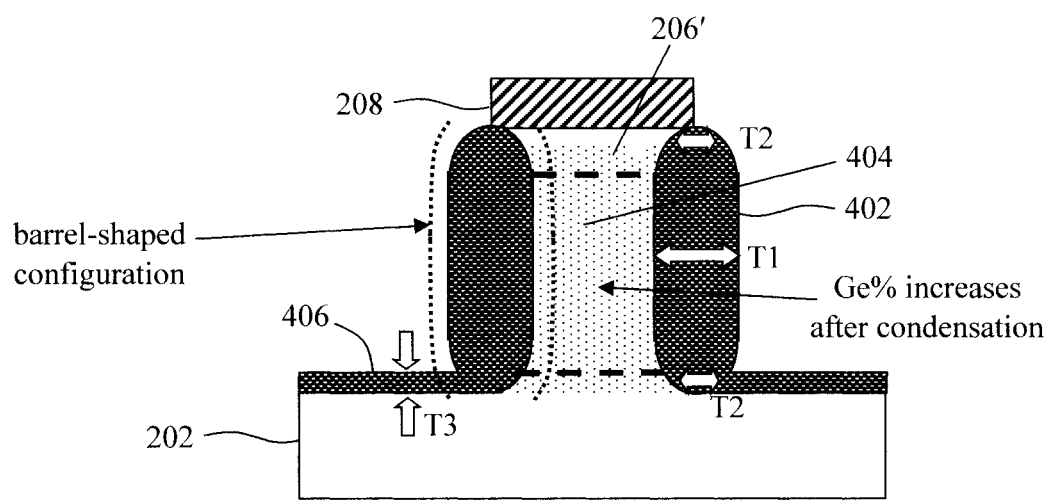
FIG. 4 is a cross-sectional diagram illustrating a thermal oxidation process having been performed to form a (barrel-shaped) oxide shell surrounding a condensed SiGe pillar core according to an embodiment of the present invention.
Figure 5:
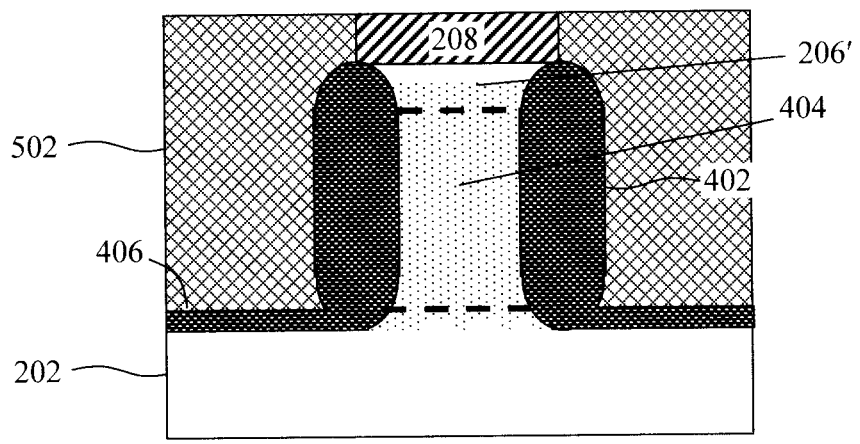
FIG. 5 is a cross-sectional diagram illustrating a supporting material having been deposited around the oxide shell according to an embodiment of the present invention.
Figure 6:
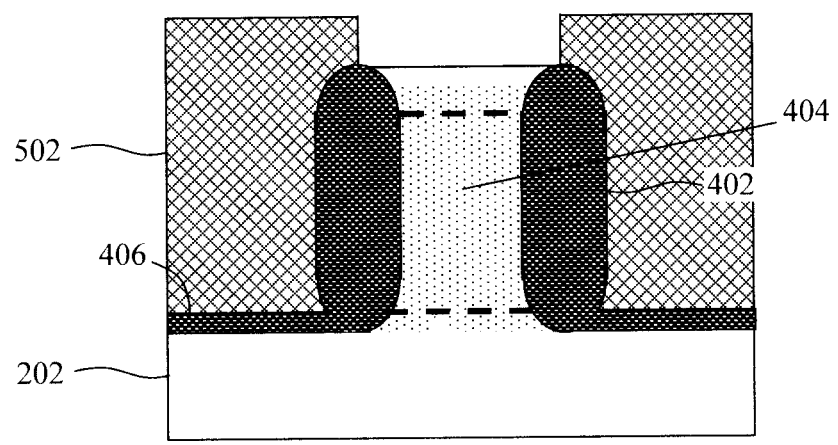
FIG. 6 is a cross-sectional diagram illustrating the hardmask having been selectively removed according to an embodiment of the present invention.

As shown in FIG. 4, the above-described thermal oxidation process is then performed in which the Si atoms in the SiGe pillar 302 are oxidized to form an oxide shell 402 on the sidewalls of a SiGe pillar core 404. As provided above, this oxidation process is carried out by annealing the SiGe pillar 302 in an oxygen ambient under conditions (oxidation species, temperature, duration, etc.) sufficient to form the oxide (i.e., SiOx or SiGeOx) shell 402 and the SiGe pillar core 404 surrounded by the oxide shell 402. According to an exemplary embodiment, the conditions comprise a temperature of from about 400° C. to about 1200° C. and ranges therebetween, and a duration of from about 1 second to about 1 hour and ranges therebetween. In some embodiments with high temperature (e.g., above 1000° C.), by way of this process, Ge atoms in SiGe pillar 302 will be pushed inwards, resulting in an increase in Ge % in the SiGe pillar core 404 as compared to the (as-patterned) SiGe pillar 302. As a result, a barrel-shaped SiOx shell is formed. For instance, by way of example only, the as-patterned SiGe pillar 302 prior to oxidation can have a Ge % of from about 20% Ge to about 50% Ge and ranges therebetween. Following the oxidation process (condensation), the SiGe pillar core 404 can have a Ge % of from about 50% Ge to about 100% Ge (i.e., pure Ge) and ranges therebetween. In other embodiments, the SiGe pillar 302 has a varied Ge % and the oxidation is performed at a low temperature (e.g., 600° C. with water vapor as oxidation species), and the lower Ge % at the top and the bottom of the SiGe pillar 302 results in less oxidation at top and bottom and more oxidation at the middle of the SiGe pillar 302. As a result, a barrel-shaped SiGeOx shell is formed.

As shown in FIG. 4, as the oxide (e.g., SiOx) shell 402 is formed, Ge in the SiGe pillar core 404 is pushed inward resulting in an increase of the Ge % in the SiGe pillar core 404. If the (optional) Si layer 206' is present on top of the SiGe pillar core 404 Si layer 206' will help to ensure that the oxide shell 402 is thicker along a middle portion of the sidewall of the SiGe pillar core 404, than along the sidewall at the top and bottom of the SiGe pillar core 404. Namely, as shown in FIG. 4, the oxide shell 402 has a thickness T1 along a middle portion of the sidewall of the SiGe pillar core 404, and a thickness T2 along the sidewall at the top and bottom of the SiGe pillar core 404, wherein T1>T2. This configuration of the oxide shell 402 can be produced even if the Si layer 206' is not present. However, having Si layer 206' to repel the Ge in the SiGe pillar core 404 during condensation will enhance the effect of pushing the Ge in the SiGe pillar core 404 inward to help create oxide shell 402 that is thicker along a middle portion of the sidewall of the SiGe pillar core 404 than along the sidewall at the top and bottom of the SiGe pillar core 404. This is due to the enhanced oxidation of SiGe as compared to Si. As such, it can be seen in FIG. 4 that an oxide layer 406 is also formed in the exposed top surface of the substrate 202 by this oxidation process when the substrate 202 is a semiconductor (e.g., silicon). However, that oxide layer 406 is thinner than the oxide (i.e., SiOx) shell 402 surrounding the SiGe pillar core 404 due to the enhanced oxidation of SiGe (i.e., in the SiGe pillar core 404) as compared to Si (in the substrate 202). For instance, oxide layer 406 has a thickness T3, wherein T3<T2<T1.

As will be described in detail below, having an oxide shell 402 that is thicker along a middle portion of the sidewall of the SiGe pillar core 404 than along the sidewall at the top and bottom of the SiGe pillar core 404 will produce a nanopore that has a wider opening at the ends of the nanopore as compared to a center of the nanopore. This oxidation also reduces the surface roughness of the SiGe pillar core 404, advantageously resulting in smoother nanopore sidewalls.

As shown in FIG. 4, oxide shell 402 has a unique configuration on each side of the SiGe pillar core 404 where the sidewalls of the oxide shell 402 slope inward at the top and at the bottom of the oxide shell 402. This is what is referred to herein as 'barrel-shaped' (see the barrel shape of oxide shell 402 depicted with dotted lines in FIG. 4). As highlighted above, this barrel shaped configuration will result in the formation of a nanopore that has a wider opening at the ends of the nanopore as compared to a center of the nanopore.

A supporting material 502 is then deposited around the oxide shell 402. See FIG. 5. Suitable supporting materials 502 include, but are not limited to, SiOx, silicon oxynitride (SiON) and/or silicon oxycarbonitride (SiOCN). A process such as chemical vapor deposition (CVD), atomic layer deposition (ALD) or physical vapor deposition (PVD) can be employed to deposit the supporting material 502. Following deposition, the supporting material 502 is planarized using a process such as chemical mechanical polishing (CMP), exposing the hardmask 208. Supporting material 502 will act as a supporting structure for the oxide shell 402 after the hardmask 208, SiGe pillar core 404, etc. are removed (see below).

Namely, the hardmask 208 is then selectively removed. See FIG. 6. For instance, as provided above, hardmask 208 can be formed from a nitride material such as SiN, SiON and/or SiCN. In that case, a nitride-selective etch can be employed to remove the hardmask 208. Removal of the hardmask 208 exposes the underlying SiGe pillar core 404. The optional Si layer 206', if present, can also be removed by selective etch such as reactive ion etch (RIE) or wet etch such as an aqueous solution containing ammonia.

Figure 7:
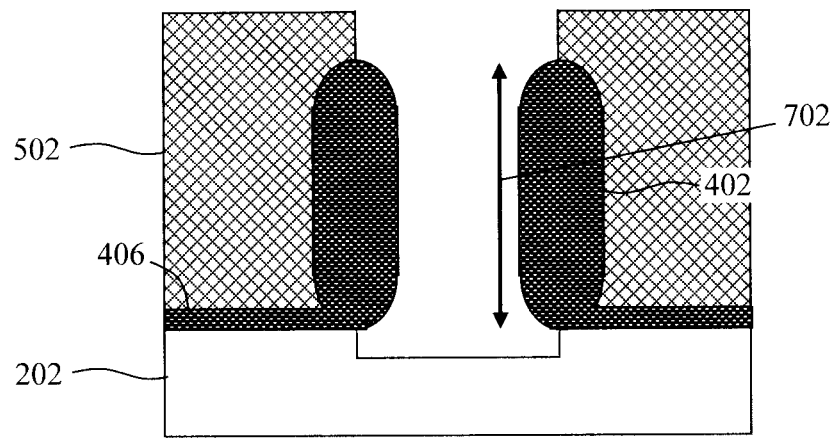
FIG. 7 is a cross-sectional diagram illustrating the SiGe pillar core having been removed selective to the oxide shell forming a nanopore surrounded by the oxide shell according to an embodiment of the present invention.

The SiGe pillar core 404 is then removed selective to the oxide shell 402. See FIG. 7. As provided above, etchants such as an aqueous solution containing ammonium and hydrogen peroxide, gas phase HCl, vapor phase $ClF_3$ and other reactive clean processes (RCP) can be employed to etch SiGe selective to Si. As shown in FIG. 7, removal of SiGe pillar core 404 forms a nanopore 702 surrounded by oxide shell 402. Supporting material 502 surrounds the oxide shell 402 and provides structural stability to the oxide shell 402.

Figure 8:
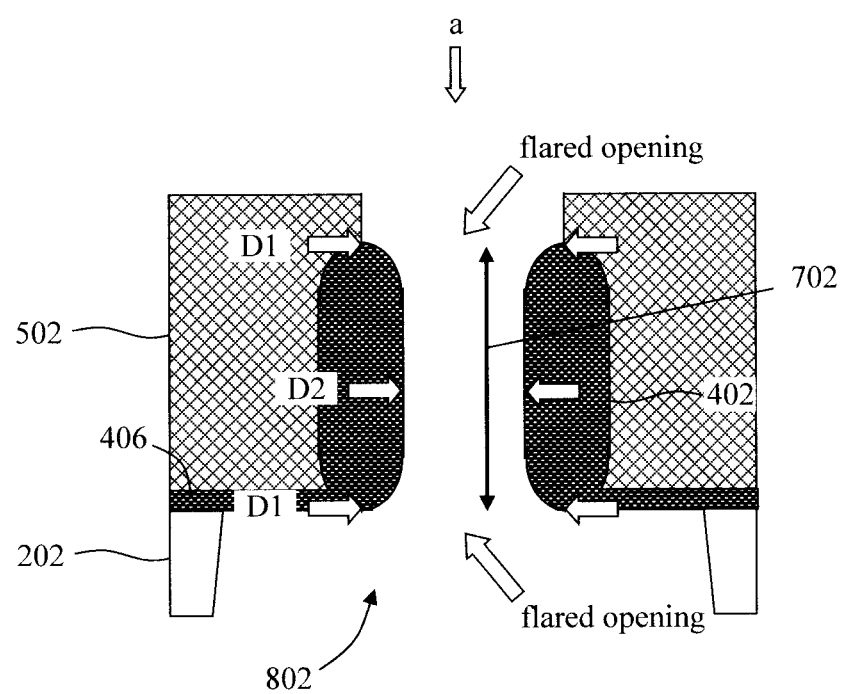
FIG. 8 is a cross-sectional diagram illustrating the substrate having been patterned to open a back side of the nanopore according to an embodiment of the present invention.

The substrate 202 is then patterned to open a back side of the nanopore 702. See FIG. 8. Namely, as shown in FIG. 8, a well 802 is patterned in the substrate 202 aligned with a (bottom) opening of the nanopore 702. Lithography and etching techniques can be employed to form well 802 in substrate 202 using, e.g., a directional etching process such as RIE. The nanopore 702 is now open at both of its ends.

Figure 8A:
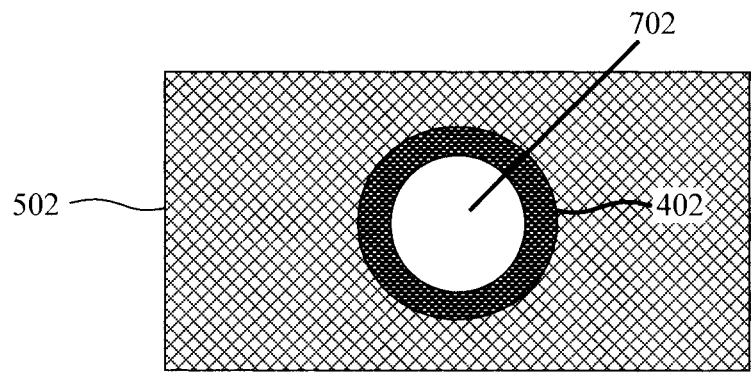
FIG. 8A is a top-down diagram illustrating that the nanopore has a cylindrical shape and is fully surrounded by the oxide shell according to an embodiment of the present invention.

Nanopore 702 has a unique structure. Namely, referring briefly to a top-down view (i.e., from view point 'a') of the nanopore structure shown in FIG. 8A, it can be seen that nanopore 702 generally has a cylindrical shape and is fully surrounded by oxide (i.e., SiOx) shell 402. Further, a diameter of nanopore 702 at the top and bottom openings of nanopore 702 is greater than the diameter at the center of nanopore 702. For instance, referring back to FIG. 8, the (top and bottom) openings on both ends of the nanopore have a diameter D1, and the center of nanopore 702 has a diameter D2, wherein D1>D2. To look at it another way, nanopore 702 has a flare at both of its (top and bottom) openings. This flared design is created by the unique 'barrel-shaped' configuration of the oxide shell 402 on each side of the nanopore 702 where the sidewalls of the oxide shell 402 slope inward at both ends (i.e., at the top and at the bottom) of the nanopore 702. By way of example only, in one exemplary embodiment, D1 is from about 15 nm to about 50 nm and ranges therebetween, and D2 is from about 5 nm to about 10 nm and ranges therebetween.

Such a flared design provides some notable advantages. For instance, the present nanopore structure can be implemented in a sensor device such as a nanopore deoxyribonucleic acid (DNA) sensor. See nanopore DNA sensor 902 shown in FIG. 9. In that case, the larger flared openings at the ends of the nanopore 702 facilitate introduction of the DNA molecules into and through the nanopore 702 for sensing.

Figure 9:
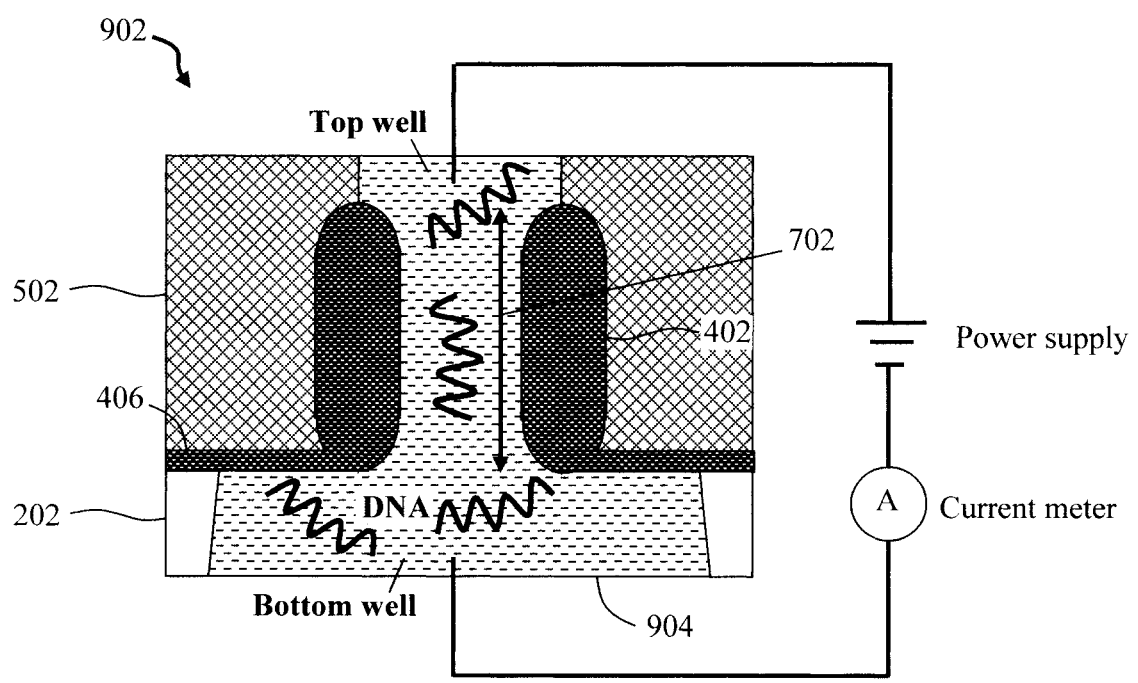
FIG. 9 is a cross-sectional diagram illustrating a nanopore sensor implementing the present nanopore structure according to an embodiment of the present invention.

As shown in FIG. 9, the opening at the top of the nanopore 702 (once occupied by the hardmask 208—see above) forms a first/top well at a first end of the nanopore 702, and the well 802 formed in substrate 202 (see above) forms a second/bottom well at a second end of the nanopore 702 opposite the first end. The top well, the nanopore 702, and the bottom well are filled with an electrolyte solution 904, such as a salt solution. The electrolyte solution 904 contains DNA molecules (or other molecules of interest).

A power supply is contact with the electrolyte solution in the top well and the bottom well on opposite ends of the nanopore 704. A current meter measures the ion current through the nanopore 702. Namely, when DNA is absent from the nanopore 702, the ion current measured by the current meter is high. This is a reference current. However, when a DNA molecule passes through the nanopore 702, it reduces the ion current measured by the current meter. The amount of the ion current reduction depends on the type of DNA. For instance, nanopore DNA sensor 902 can be used for DNA sequencing where the ion current measured is indicative of particular nucleotide base pairs. The larger flared openings at the top and the bottom of the nanopore 702 facilitate the DNA molecules entering the nanopore 702 from the top well and exiting the nanopore into the bottom well, or vice versa.

Also provided herein are techniques for nanopore formation where pore size is unaffected by process variation. For instance, when conventional direct patterning techniques are employed in the formation of nanopores, it is inevitable that the dimensions (e.g., diameter) of the patterned nanopores will vary. Advantageously, it has been found herein that the nanopore size can be precisely controlled by atomic layer etch (ALE) and atomic layer deposition (ALD) such that the resulting nanopores are uniform despite process variations that occur during fabrication.

Figure 10:
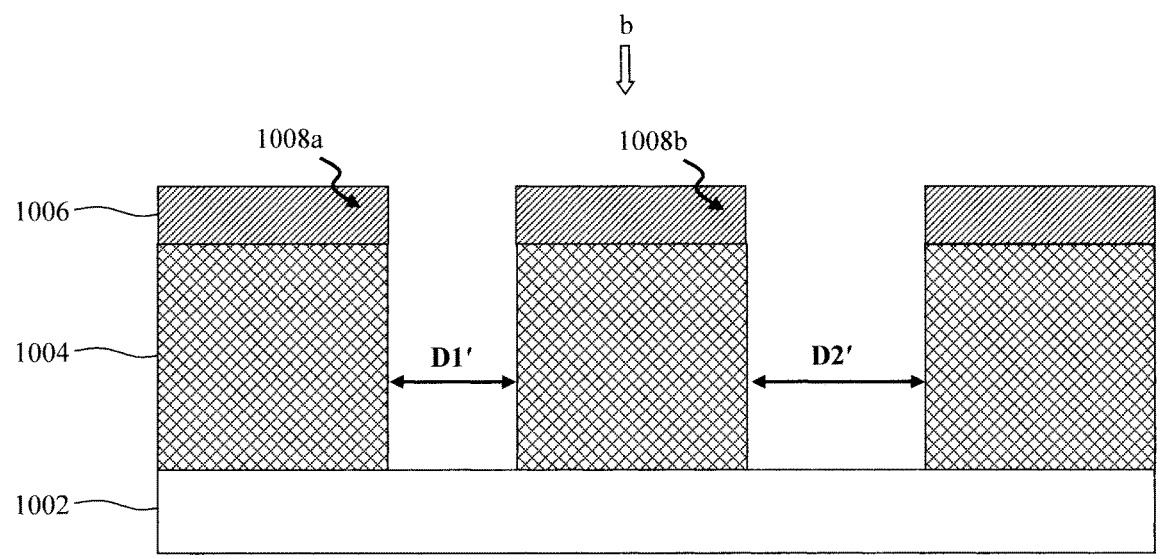
FIG. 10 is a cross-sectional diagram illustrating, according to an alternative embodiment, a first film and a second film having been deposited on a substrate, and (first, second, etc.) pores having been patterned in the first film and the second film according to an embodiment of the present invention.

For instance, an exemplary methodology for formation of a nanopore structure according to another exemplary embodiment is now described by way of reference to FIGS. 10-20. As shown in FIG. 10, the process begins with a substrate 1002 on which a first film 1004 and a second film 1006 are deposited, and a (first, second, etc.) pore 1008a, 1008b, etc. having been patterned in the first film 1004 and second film 1006.

According to an exemplary embodiment, substrate 1002 is a bulk semiconductor wafer, such as a bulk Si, bulk Ge, bulk SiGe and/or bulk III-V semiconductor wafer. Alternatively, substrate 1002 can be an SOI wafer. The SOI layer can include any suitable semiconductor, such as Si, Ge, SiGe, and/or a III-V semiconductor. Substrate 1002 may already have pre-built structures (not shown) such as transistors, diodes, capacitors, resistors, interconnects, wiring, etc.

First film 1004 and second film 1006 are each formed from a material that can be etched selective to the other. By way of example only, nitride and oxide materials provide this required etch selectivity. Suitable nitride materials include, but are not limited to, silicon nitride (SiN) and/or silicon carbide nitride (SiCN). Suitable oxide materials include, but are not limited to, SiOx and/or silicon oxycarbide (SiCO). For instance, in one exemplary embodiment, first film 1004 is formed from an oxide material such as SiOx and second film 1006 is formed from a nitride material such as SiN. Alternatively, first film 1004 can be formed from a nitride material such as SiN and second film 1006 can be formed from an oxide material such as SiOx.

A process such as CVD, ALD or PVD can be employed to deposit the first film 1004 on substrate 1002 and the second film 1006 on first film 1004. According to an exemplary embodiment, first film 1004 has a thickness of from about 10 nm to about 20 nm and ranges therebetween, and second film 1006 has a thickness of from about 2 nm to about 5 nm and ranges therebetween.

Lithography and etching techniques are then employed to pattern pores 1008a, 1008b, etc. extending through the first film 1004 and second film 1006 using, e.g., a directional etching process such as RIE. For ease and clarity of depiction, two pores 1008a and 1008b are shown in FIG. 10. However, it is to be understood that the number of pores can vary and embodiments are contemplated herein where a different number of pores are formed in first film 1004/second film 1006 than shown in the figures, including scenarios where a single pore is formed.

As shown in FIG. 10, it is likely that there will be some size variation amongst the pores 1008a, 1008b, etc. For instance, pore 1008a has a diameter D1' and pore 1008b has a diameter D2', wherein D2'>D1'. By way of example only, D1' can be from about 10 nm to about 15 nm and ranges therebetween, and D2' can be from about 15 nm to about 20 nm and ranges therebetween. What is notable, however is that these pore 1008a and pore 1008b have some size differences due to variations in the patterning process.

Figure 11:
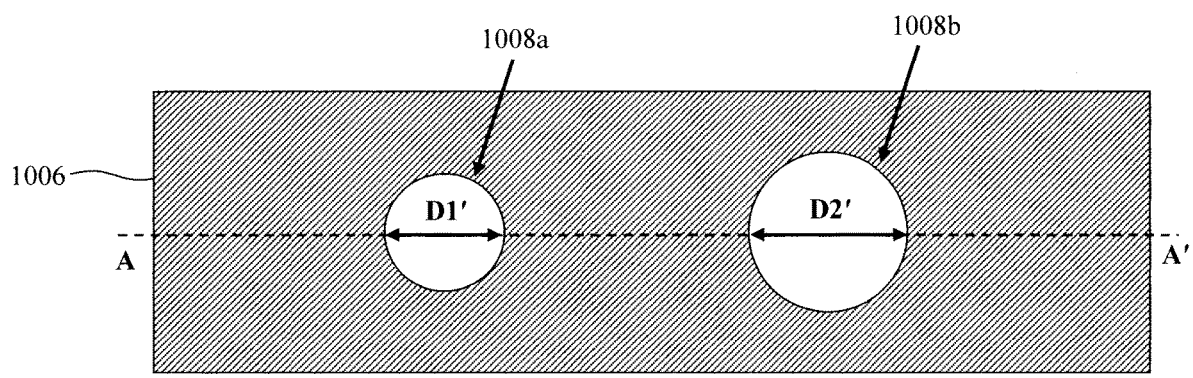
FIG. 11 is a top-down diagram illustrating that the first and second pores can vary in size (e.g., diameter) according to an embodiment of the present invention.

These process variations are further illustrated in FIG. 11 which provides a top-down view (e.g., from viewpoint b—see FIG. 10) of the structure at this stage in the fabrication process. To look at it another way, FIG. 10 is a cross-sectional view A-A' through FIG. 11. As shown in FIG. 11, pore 1008a has a diameter D1' and pore 1008b has a diameter D2', wherein D2'>D1'. Advantageously, the present techniques are unaffected by these variations in pore diameter, and will produce nanopores having a uniform size.

Figure 12:
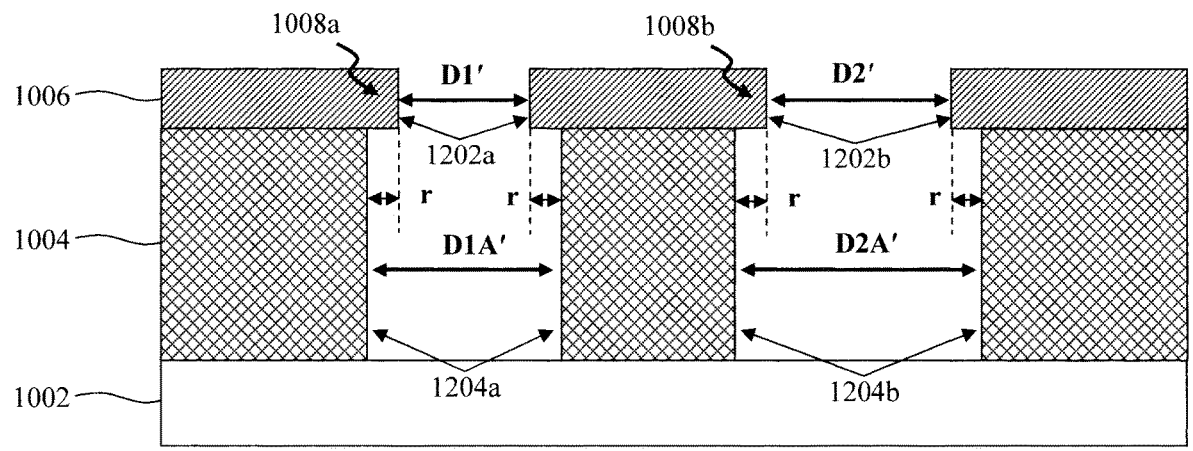
FIG. 12 is a cross-sectional diagram illustrating a selective atomic layer etch (ALE) of the first film having been performed to enlarge the first and second pores in the first film according to an embodiment of the present invention.

Next, a selective etch process such as atomic layer etch (ALE) of the first film 1004 is performed to enlarge the pores 1008a and 1008b in the first film 1004. See FIG. 12. As shown in FIG. 12, the ALE enlarges the radius of the pores 1008a and 1008b by an amount r. As will become apparent from the description that follows, r is equivalent to the radius of the final nanopores that will be produced. For instance, by way of example only, if r=3 nm, then the diameter of the final nanopore size would be 2r=6 nm. Atomic layer etching or ALE is a self-limiting etch technique for removing thin layers of a material using sequential reaction steps. ALE enables the precise removal of individual atomic layers of a material. While ALE removes material, the equivalent process atomic layer deposition or ALD uses sequential, self-limiting reaction steps to deposit a material onto a surface. Besides ALE, other etch processes such as chemical oxide removal (COR) can be used to precisely etch the first film 1004 when it is an oxide.

As shown in FIG. 12, following the etch step, the second film 1006 overhangs the pores 1008a and 1008b, creating an opening to the pores 1008a and 1008b that is smaller than the (enlarged) pores 1008a and 1008b themselves. Namely, following enlargement, pores 1008a and 1008b now have diameters D1A' and D1B' in first film 1004, while the diameters of pores 1008a and 1008b in the second film 1006 remains at D1' (wherein D1A'>D1' by an amount r) and D2' (wherein D2A'>D2' by an amount r), respectively. That way, when a conformal dielectric material is next deposited into the pores 1008a and 1008b, the dielectric material will pinch off the openings to the pores 1008a and 1008b in the second film 1006 before the dielectric material fully fills the pores 1008a and 1008b, leaving voids in pores 1008a and 1008b. These voids are the nanopores.

Notably, the nanopores formed by this process will have a uniform size (i.e., 2r—see above) regardless of the variations in the diameter of the starting pores 1008a and 1008b. To understand this concept, it is important to note that the radius of both pores 1008a and 1008b is enlarged by the same amount r. See FIG. 12. When the dielectric material is then conformally deposited into the pores 1008a and 1008b (by ALD) including on surfaces 1204a,b of first film 1004 and surfaces 1202a,b of second film 1006, the thickness of the material deposited onto these surfaces will build uniformly towards the center of pores 1008a and 1008b, respectively. Given that the radius of the pores 1008a and 1008b have been enlarged by amount r, the pore openings in second film 1006 will be pinched off while a void (with a diameter 2r) remains in the center of each of the pores 1008a and 1008b. This result occurs regardless of the variations in the diameter of the starting pores 1008a and 1008b, i.e., the voids created at the center of each of the pores 1008a and 1008b will each have a diameter 2r. Namely, in the present example, pore 1008b is larger than pore 1008a. Thus, a larger amount of the dielectric material needs to be built up along the sidewalls of pore 1008b to create a void at the center with a diameter 2r. However, due to the relatively larger opening over pore 1008b, deposition of the dielectric material into pore 1008b can continue even after the smaller pore 1008a has already been pinched-off.

Figure 13:
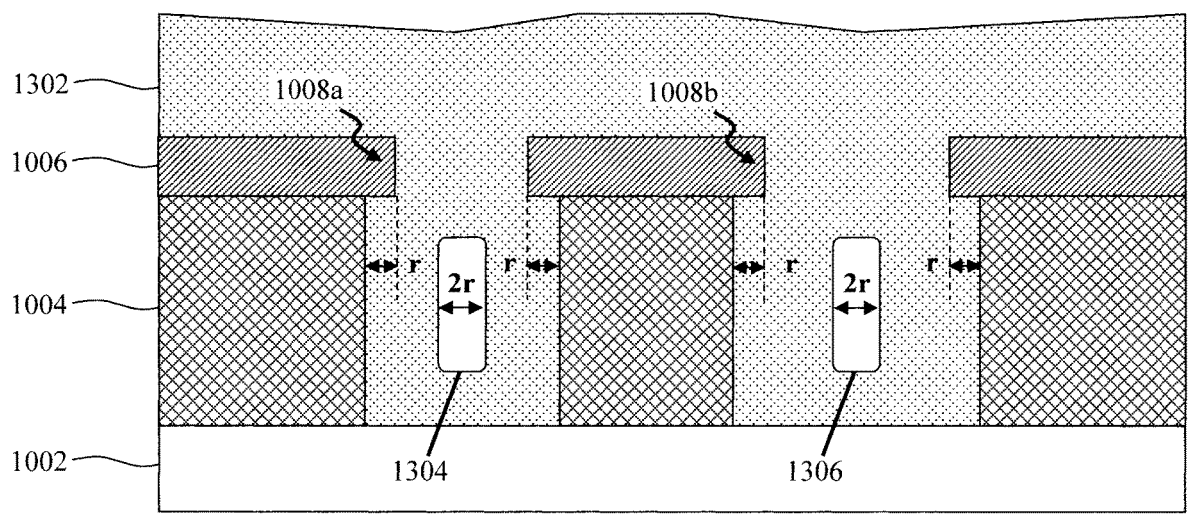
FIG. 13 is a cross-sectional diagram illustrating a dielectric material having been deposited into the first and second pores by atomic layer deposition (ALD) that pinches off the pore openings in the second film forming (first, second, etc.) nanopores in the center of the dielectric material in each of first and second pores according to an embodiment of the present invention.

Namely, as shown in FIG. 13, a film of the dielectric material 1302 has been deposited into the pores 1008a and 1008b by ALD that pinches off the pore openings in the second film 1006. Some examples of the dielectric material 1302 include, but are not limited to, silicon nitride (SiN), silicon carbide (SiC), silicon oxynitride (SiON), carbon-doped silicon oxide (SiOC), silicon-carbon-nitride (SiCN), boron nitride (BN), silicon boron nitride (SiBN), silicoboron carbonitride (SiBCN), silicon oxycabonitride (SiOCN), silicon oxide, hafnium oxide, hafnium silicon oxide, hafnium silicon oxynitride, lanthanum oxide, lanthanum aluminum oxide, zirconium oxide, zirconium silicon oxide, zirconium silicon oxynitride, tantalum oxide, titanium oxide, barium strontium titanium oxide, barium titanium oxide, strontium titanium oxide, yttrium oxide, and/or aluminum oxide. The dielectric material 1302 can be formed by any suitable techniques such as atomic layer deposition (ALD), or molecular layer deposition (MLD). As a result of this process, voids are created forming nanopores 1304 and 1306 in the center of the dielectric material 1302 in each of pores 1008a and 1008b, respectively, each having a diameter 2r. See FIG. 13.

Figure 14:
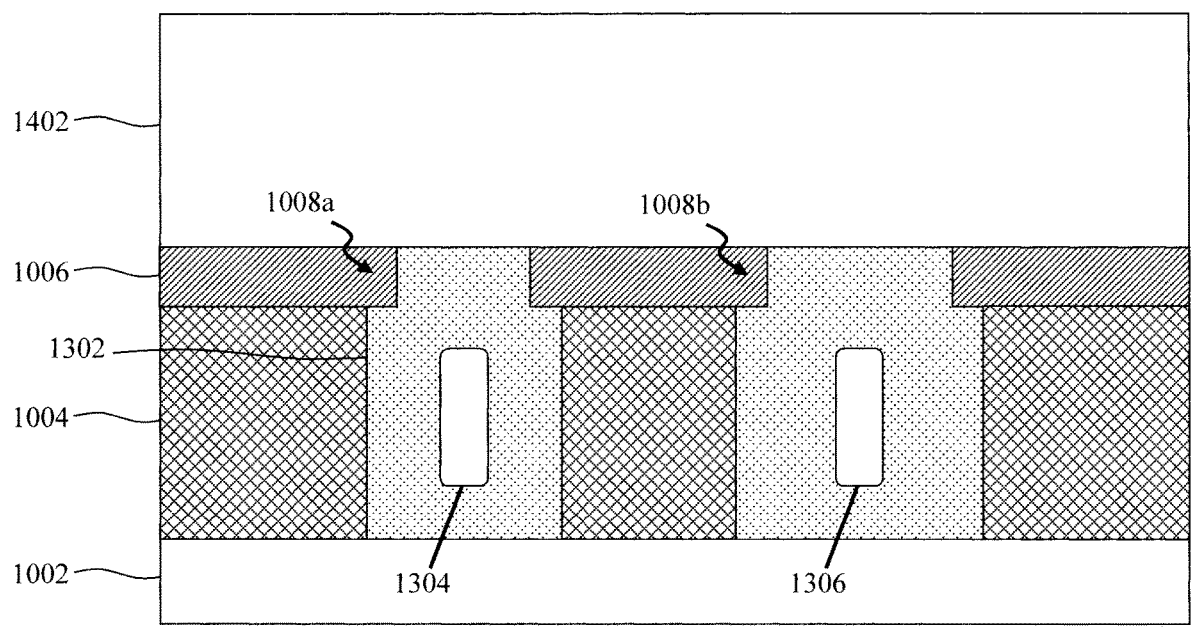
FIG. 14 is a cross-sectional diagram illustrating the dielectric material having been polished down to the second film, and a top well layer having been deposited on the second film over the dielectric material/nanopores according to an embodiment of the present invention.
Figure 15:
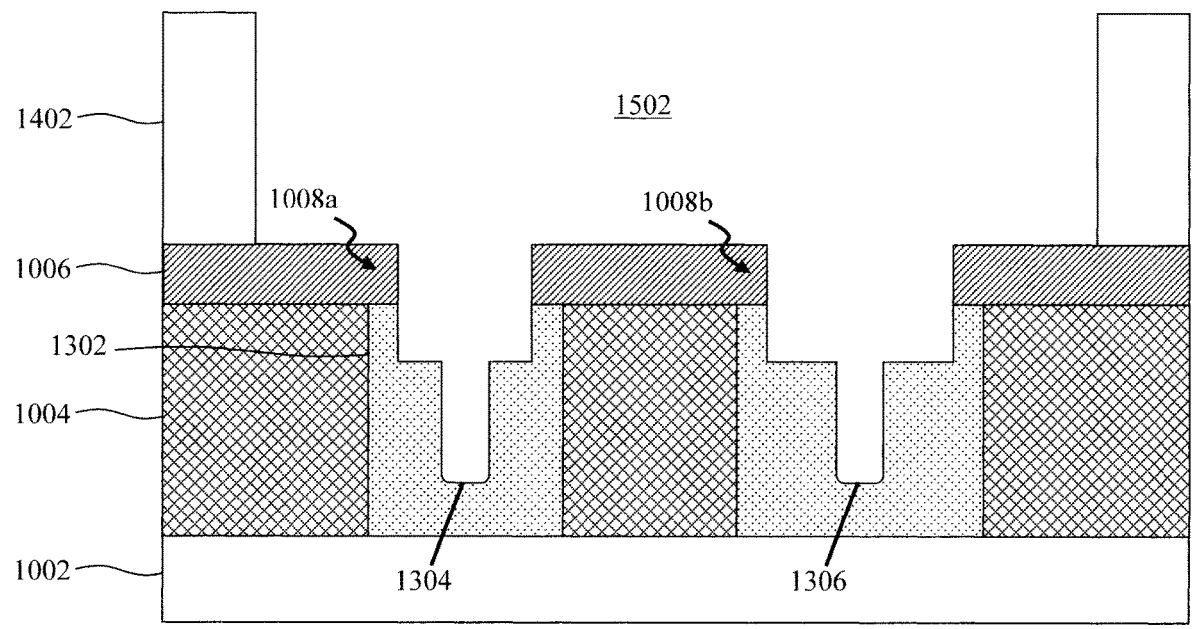
FIG. 15 is a cross-sectional diagram illustrating a top well having been formed in the top well layer which opens up the tops of the first and second nanopores according to an embodiment of the present invention.
Figure 16:
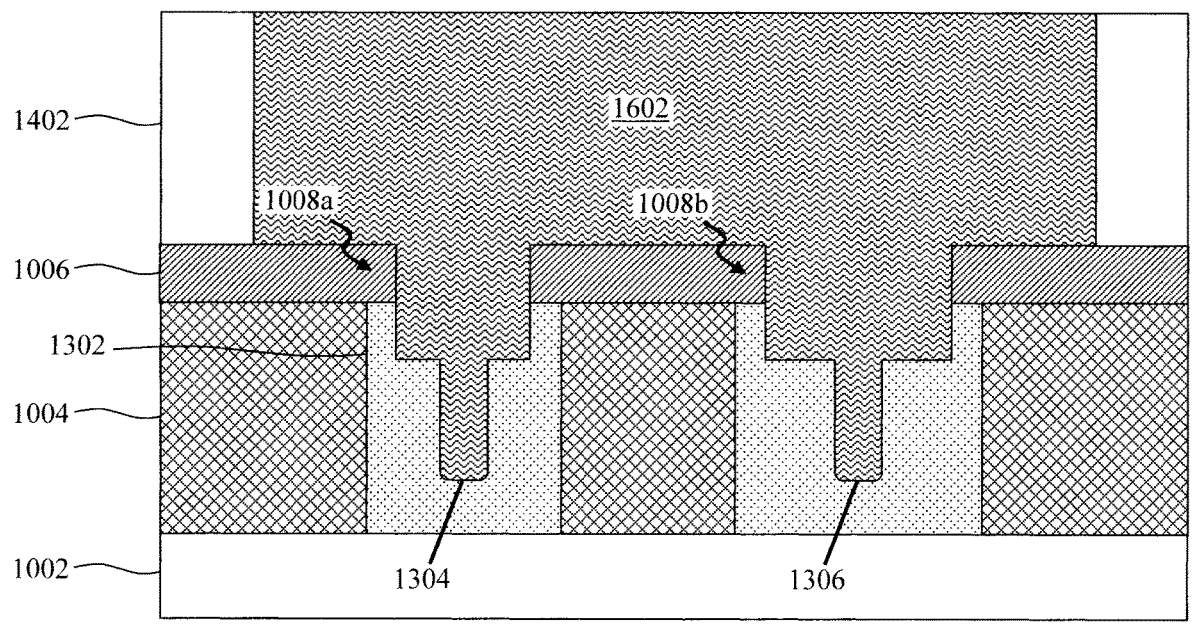
FIG. 16 is a cross-sectional diagram illustrating a sacrificial material having been deposited into and filling the top well and the first and second nanopores according to an embodiment of the present invention.
Figure 17:
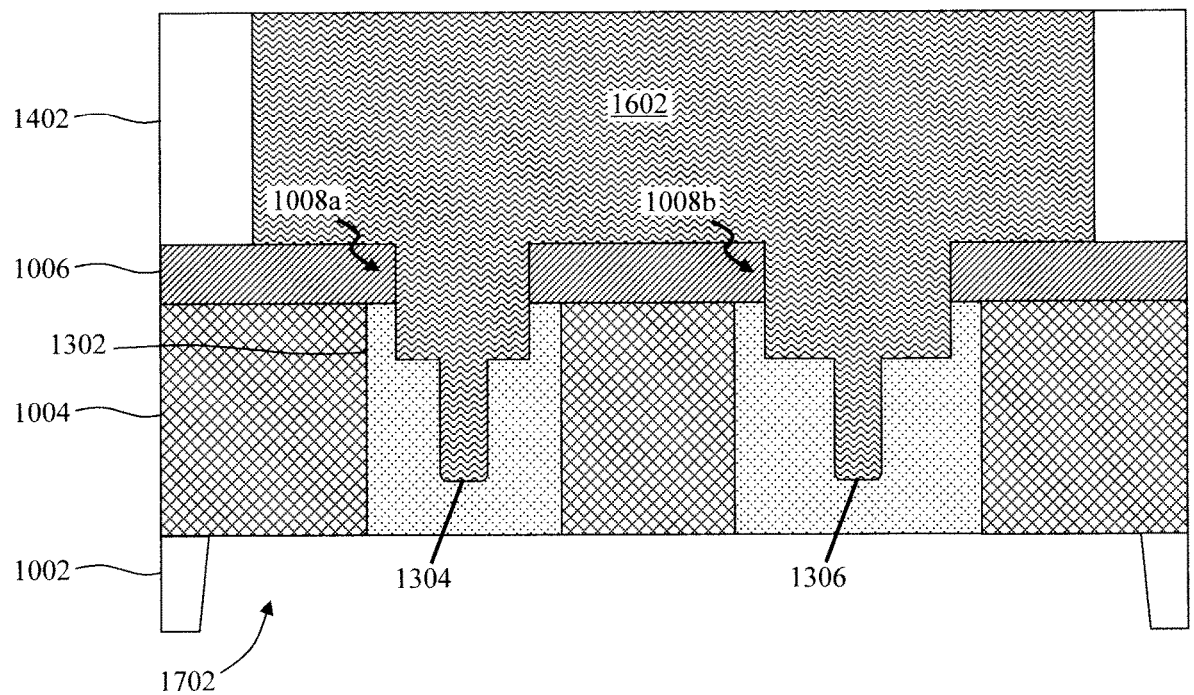
FIG. 17 is a cross-sectional diagram illustrating the substrate having been patterned to form a bottom well below the first and second nanopores according to an embodiment of the present invention.

The dielectric material 1302 is then planarized, e.g., using a process such as CMP, stopping on the second film 1006. See FIG. 14. As shown in FIG. 14, the top surface of the polished dielectric material 1302 is now coplanar with the top surface of the second film 1006.

Steps are then performed to open the ends at the tops and bottoms of the nanopores 1304 and 1306. In the example that follows, the nanopores 1304 and 1306 will be used to form a nanopore sensor. However, the present techniques can be applied to any type of nanopore structure. To open the tops of nanopores 1304 and 1306, a top well layer 1402 is first deposited on the second film 1006 over dielectric material 1302/nanopores 1304 and 1306. Suitable materials for top well layer 1402 include, but are not limited to, oxide materials such as SiOx SiCO, SiON and/or SiOCN. A process such as CVD, ALD or PVD can be employed to deposit the top well layer 1402. According to an exemplary embodiment, top well layer 1402 has a thickness of from about 10 nm to about 20 nm and ranges therebetween.

Lithography and etching techniques using, e.g., a directional etching process such as RIE are then employed to form at least one (top) well 1502 in top well layer 1402 above the nanopores 1304 and 1306. See FIG. 15. In the present example, the nanopores 1304 and 1306 will share a common top well 1502. However, embodiments are contemplated herein where multiple wells are formed in top well layer 1402, such as where a different well is formed over each of nanopores 1304 and 1306. During the patterning of top well 1502, dielectric material 1302 is etched through the pore openings in second film 1006 to open up the tops of nanopores 1304 and 1306. As will be described in detail below, this process will create a unique nanopore structure.

A sacrificial material 1602 is then deposited into and filling top well 1502 and nanopores 1304 and 1306. See FIG. 16. The term 'sacrificial' as used herein refers to a structure that is removed, in whole or in part, during fabrication of the nanopore structure. In this case, sacrificial material 1602 will be removed after opening the bottoms of the nanopores 1304 and 1306. Thus, sacrificial material 1602 needs to be removable/etchable selective to dielectric material 1302. Suitable sacrificial materials 1602 include, but are not limited to, amorphous carbon. A process such as plasma enhanced CVD (PECVD) can be employed to deposit the sacrificial material 1602.

The substrate 1002 is then patterned to form a bottom well 1702 below the nanopores 1304 and 1306. See FIG. 17. Lithography and etching techniques can be employed to form bottom well 1702 in substrate 1002 using, e.g., a directional etching process such as RIE. Following formation of the bottom well 1702, the bottoms of the nanopores 1304 and 1306 still remain covered by the dielectric material 1302.

Figure 18:
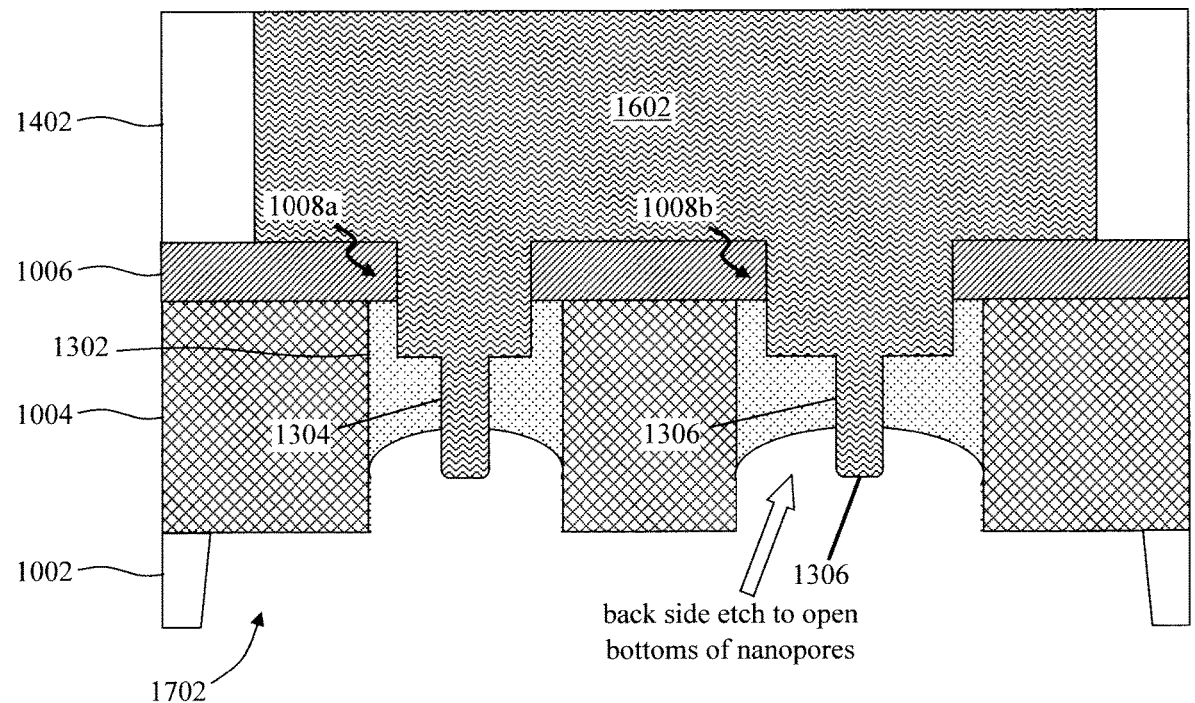
FIG. 18 is a cross-sectional diagram illustrating a selective etch back from the back side of the dielectric material having been performed through the bottom well to open up the bottoms of the first and second nanopores according to an embodiment of the present invention.

Thus, a selective etch back from the back side of dielectric material 1302 is next performed through the bottom well 1702 to open up the bottoms of the nanopores 1304 and 1306. See FIG. 18. As shown in FIG. 18, this back side etch of dielectric material 1302 exposes the sacrificial material 1602 in nanopores 1304 and 1306. According to an exemplary embodiment, a non-directional (isotropic) etching process is employed for the etch back.

Figure 19:
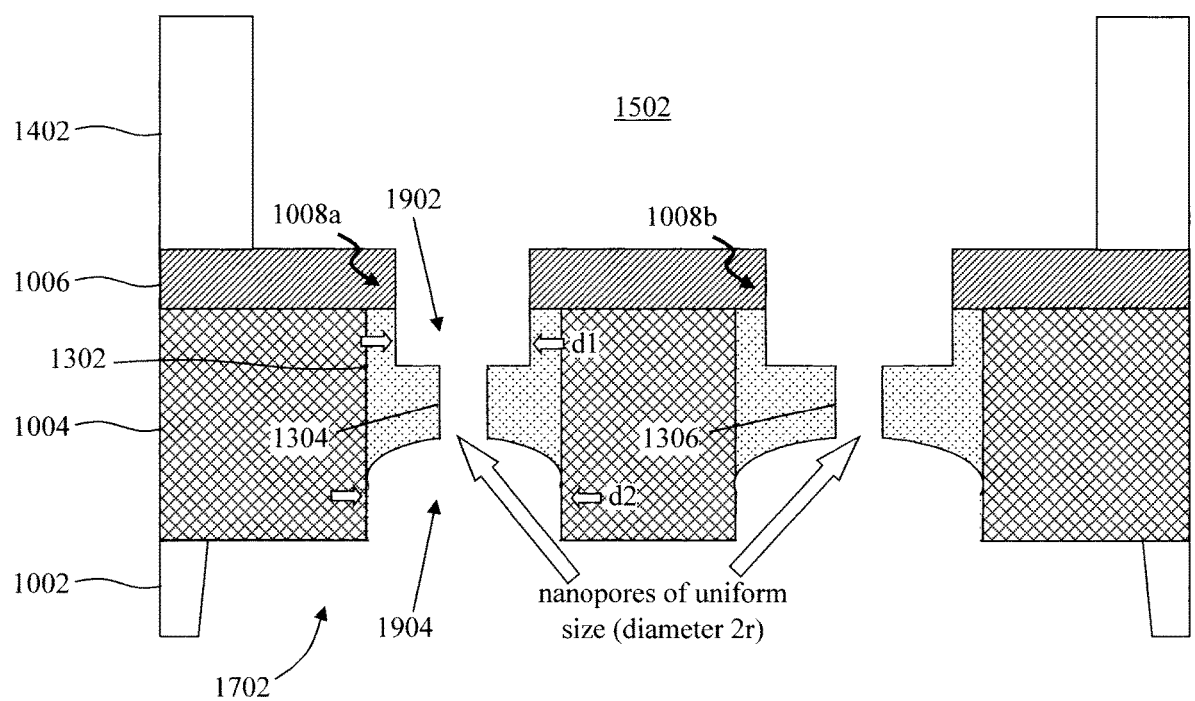
FIG. 19 is a cross-sectional diagram illustrating the sacrificial material having been removed to expose the first and second nanopores according to an embodiment of the present invention.

The sacrificial material 1602 is then removed to expose the nanopores 1304 and 1306. See FIG. 19. As provided above, sacrificial material 1602 can be amorphous carbon. In that case, an oxygen plasma etch or ozone ashing process etch can be employed to remove sacrificial material 1602. As shown in FIG. 19, the present fabrication process results in the formation of a unique nanopore structure. First, as described in detail above, regardless of the starting pore size, the resulting nanopores 1304 and 1306 have a uniform size (i.e., a uniform diameter 2r).

Further, opening the tops of the nanopores 1304 and 1306 during patterning of the first well through the pore openings in the second film 1006, and opening the bottoms of the nanopores 1304 and 1306 by a back side etch results in a unique configuration of the dielectric material 1302 at opposite ends of the nanopores 1304 and 1306. For instance, as shown in FIG. 19, a top opening 1902 to the nanopores 1304 and 1306 has a first diameter d1 (based on smaller pore openings in the second film 1006), and a bottom opening 1904 to the nanopores 1304 and 1306 has a second diameter d2, wherein d2>d1.

Figure 20:
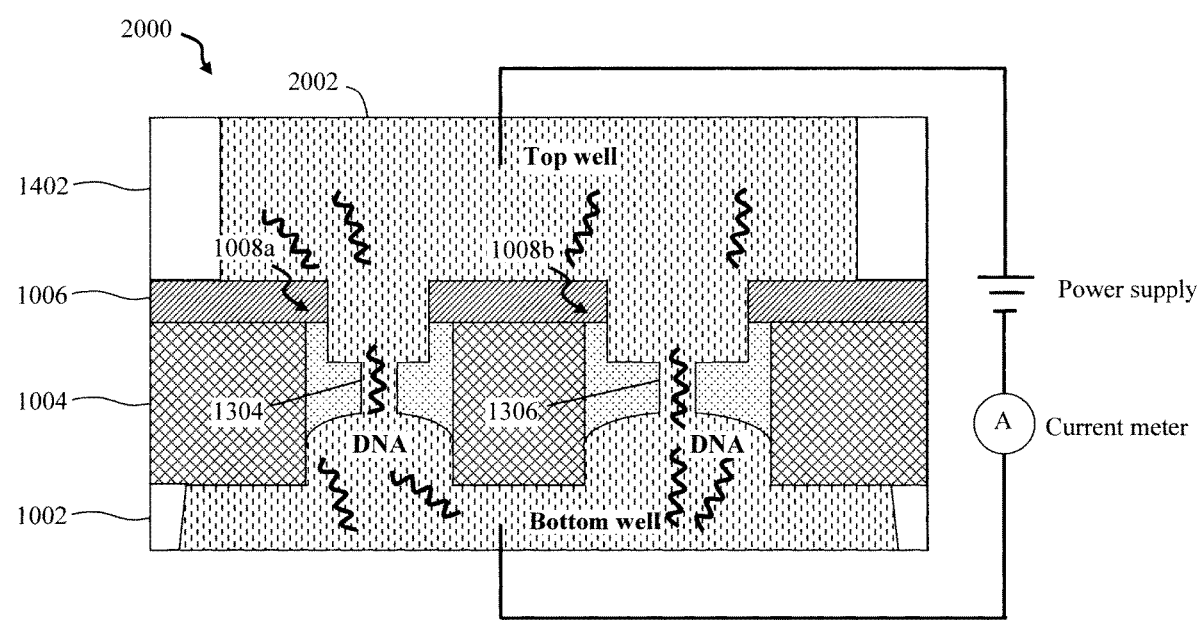
FIG. 20 is a cross-sectional diagram illustrating another nanopore sensor implementing the present nanopore structure according to an embodiment of the present invention.

In one exemplary embodiment, the present nanopore structure is implemented in a sensor device such as a DNA sensor. See nanopore DNA sensor 2000 shown in FIG. 20. As shown in FIG. 20, the top well 1502, the nanopores 1304 and 1306, and the bottom well 1702 are filled with an electrolyte solution 2002, such as a salt solution. In this example, the electrolyte solution 2002 contains DNA molecules (or other molecules of interest).

A power supply is contact with the electrolyte solution in the top well 1502 and the bottom well 1702 on opposite ends of the nanopores 1304 and 1306. A current meter measures the ion current through the nanopores 1304 and 1306. Namely, when DNA is absent from the nanopores 1304 and 1306, the ion current measured by the current meter is high. This is a reference current. However, when a DNA molecule passes through the nanopores 1304 and 1306, it reduces the ion current measured by the current meter. The DNA molecules can enter the nanopores 1304 and 1306 from the top well 1502 and exit the nanopores 1304 and 1306 in the bottom well 1702, or vice versa. The amount of the ion current reduction depends on the type of DNA. For instance, nanopore DNA sensor 2000 can be used for DNA sequencing where the ion current measured is indicative of particular nucleotide base pairs.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method of forming a nanopore structure, the method comprising:
    forming a silicon germanium (SiGe) pillar on a substrate;
    annealing the SiGe pillar in an oxygen-containing ambient under conditions sufficient to form an oxide shell surrounding a condensed SiGe pillar core; and
    removing the condensed SiGe pillar core selective to the oxide shell to form a nanopore in the oxide shell.

2. The method of claim 1, wherein the conditions comprise a temperature and a duration.

3. The method of claim 2, wherein the temperature is from about 400° C. to about 1200° C. and ranges therebetween, and wherein the duration is from about 1 second to about 1 hour and ranges therebetween.

4. The method of claim 1, further comprising:
depositing a SiGe layer onto the substrate;
forming a hardmask on the SiGe layer; and
patterning the SiGe layer using the hardmask to form the SiGe pillar on the substrate.

5. The method of claim 4, further comprising:
depositing a silicon (Si) layer on the SiGe layer prior to forming the hardmask on the SiGe layer.

6. The method of claim 4, wherein the SiGe layer has a germanium (Ge) percentage of from about 20% Ge to about 50% Ge.

7. The method of claim 4, wherein a Ge concentration varies within the SiGe layer.

8. The method of claim 7, wherein a highest Ge concentration within the SiGe layer is at a middle of the SiGe layer, and wherein a lowest Ge concentration within the SiGe layer is at a top and a bottom of the SiGe layer.

9. The method of claim 8, wherein the highest Ge concentration within the SiGe layer has a Ge percentage of 50%, and wherein the lowest Ge concentration within the SiGe layer has a Ge percentage of 5%.

10. The method of claim 1, wherein the oxide shell is barrel-shaped, such that the nanopore formed in the oxide shell has wider openings at ends of the nanopore as compared to at a center of the nanopore.

11. The method of claim 1, further comprising:
depositing a supporting material around the oxide shell prior to removing the condensed SiGe pillar core.

12. The method of claim 11, wherein the supporting material is selected from the group consisting of: silicon oxide (SiOx), silicon oxynitride (SiON), silicon oxycarbonitride (SiOCN), and combinations thereof.

\* \* \* \* \*